United States Patent
Andrejko et al.

(10) Patent No.: US 9,606,980 B2
(45) Date of Patent: Mar. 28, 2017

(54) GENERATING NATURAL LANGUAGE TEXT SENTENCES AS TEST CASES FOR NLP ANNOTATORS WITH COMBINATORIAL TEST DESIGN

(71) Applicant: International Business Machines Corporation, Armonk, NY (US)

(72) Inventors: Pamela D. Andrejko, Cary, NC (US); Andrew R. Freed, Cary, NC (US); Cynthia M. Murch, Pine Island, MN (US); Robert L. Nielsen, Chapel Hill, NC (US); Jan M. Nordland, Hayfield, MN (US); Humberto R. Rivero, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 174 days.

(21) Appl. No.: 14/572,691

(22) Filed: Dec. 16, 2014

(65) Prior Publication Data

US 2016/0170972 A1  Jun. 16, 2016

(51) Int. Cl.
*G06F 17/27* (2006.01)
*G06F 17/24* (2006.01)
(Continued)

(52) U.S. Cl.
CPC .......... *G06F 17/274* (2013.01); *G06F 17/241* (2013.01); *G06F 17/2735* (2013.01);
(Continued)

(58) Field of Classification Search
CPC .. G06F 17/241; G06F 17/2264; G06F 17/227; G06F 17/2276; G06F 17/2282
See application file for complete search history.

(56) References Cited

U.S. PATENT DOCUMENTS 5,491,628 A * 2/1996 Wakayama ......... G06F 17/2247
704/9
6,401,061 B1  6/2002 Zieman
(Continued)

FOREIGN PATENT DOCUMENTS

EP  0388156  9/1997

OTHER PUBLICATIONS

Google, "simplenig Section 3, Getting started" [online], retrieved on Nov. 26, 2014 from the Internet URL: https://code.google.com/p/simplenig/wiki/Section3.

(Continued)

*Primary Examiner* — Richard Zhu
(74) *Attorney, Agent, or Firm* — Diana R. Gerhardt; Jack V. Musgrove

(57) ABSTRACT

Test cases for a text annotator are generated by determining types of inputs to the annotator and analyzing language structures in a corpus to identify sentence types and grammar constructs. An input type can correspond to multiple grammar constructs. Test cases are generated by performing grammar tree transformations on selected fragments from the corpus based on the sentence types and the grammar constructs. Additional test cases are generated by replacing starting phrases in selected fragments with substitute phrases from dictionaries associated with the input types (a dictionary can include a false synonym for an input type for purposes of negative testing). The two generating approaches can be combined, i.e., performing one or more successive (different) grammar tree transformations to yield a sentence which is then subjected to phrase substitution.

18 Claims, 6 Drawing Sheets

(51) Int. Cl.
*G06F 17/28* (2006.01)
*G06F 17/22* (2006.01)
*G06F 19/00* (2011.01)

(52) U.S. Cl.
CPC ...... *G06F 17/2775* (2013.01); *G06F 17/2881* (2013.01); *G06F 17/227* (2013.01); *G06F 17/2264* (2013.01); *G06F 17/2276* (2013.01); *G06F 17/2282* (2013.01); *G06F 19/3487* (2013.01)

(56) References Cited

U.S. PATENT DOCUMENTS

| | | | | |
|---|---|---|---|---|
| 6,470,306 | B1* | 10/2002 | Pringle | G06F 17/241 |
| | | | | 704/3 |
| 6,738,738 | B2* | 5/2004 | Henton | G06F 17/273 |
| | | | | 704/2 |
| 7,392,174 | B2 | 6/2008 | Freeman | |
| 7,640,470 | B2 | 12/2009 | Lammel et al. | |
| 8,356,245 | B2 | 1/2013 | Doganata et al. | |
| 8,484,188 | B1* | 7/2013 | Upstill | G06F 17/30241 |
| | | | | 707/706 |
| 8,489,926 | B2* | 7/2013 | Kube | G06F 11/3684 |
| | | | | 714/25 |
| 8,543,906 | B2* | 9/2013 | Chidlovskii | G06F 17/2247 |
| | | | | 715/234 |
| 8,838,440 | B2 | 9/2014 | Iwama et al. | |
| 8,977,953 | B1* | 3/2015 | Pierre | G06F 17/2785 |
| | | | | 715/201 |
| 2003/0036900 | A1* | 2/2003 | Weise | G06F 17/274 |
| | | | | 704/9 |
| 2006/0245654 | A1* | 11/2006 | Viola | G06K 9/00463 |
| | | | | 382/229 |
| 2008/0082910 | A1* | 4/2008 | Nishino | G06F 17/2264 |
| | | | | 715/231 |
| 2010/0023319 | A1 | 1/2010 | Bikel et al. | |
| 2013/0035930 | A1* | 2/2013 | Ferrucci | G06F 17/30976 |
| | | | | 704/9 |
| 2013/0067311 | A1 | 3/2013 | Doganata et al. | |
| 2013/0103390 | A1* | 4/2013 | Fujita | G06F 17/2765 |
| | | | | 704/9 |
| 2013/0263089 | A1 | 10/2013 | Banerjee et al. | |
| 2014/0115438 | A1 | 4/2014 | Bhatt et al. | |
| 2014/0136188 | A1 | 5/2014 | Wroczynski et al. | |
| 2014/0163962 | A1 | 6/2014 | Castelli et al. | |

OTHER PUBLICATIONS

Hexawise, "Combinatorial Software Test Design—Beyond Pairwise Testing" [online], retrieved on Nov. 26, 2014 from the Internet URL: http://hexawise.com/2010/10/a-fun-presentation-on-a-powerful-software-test-design-approach/.

IP.com, "Test Coverage of a natural language corpus", IP.com Prior Art Database Technical Disclosure, n. 000236478 (Apr. 29, 2014).

Khosmood, Foaad, et al., "Combining Corpus-Based Features for Selecting Best Natural Language Sentences", 10th Int'l. Conf. on Machine Learning and Applications, pp. 362-365 (2011).

Satish, Preeti, et al., "Extracting the Combinatorial Test Parameters and Values from UML Sequence Diagrams", IEEE 7th Int'l. Conf. on Software Testing, Verification, and Validation Workshops, pp. 88-97 (2014).

Schneider, Nathan, et al., "A Framework for (Under) Specifying Dependency Syntax Without Overloading Annotators", Proc. 7th Linguistic Annotation Workshop (Aug. 2013).

Wikipedia, "All-pairs testing" [online], retrieved on Nov. 26, 2014 from the Internet URL: http://en.wikipedia.org/wiki/All-pairs_testing.

Zlotnick, "Combinatorial Test Design" [online], retrieved on Nov. 26, 2014 from the Internet URL: https://www.research.ibm.com/haifa/dept/svt/papers/CTD_Introduction.pdf.

* cited by examiner

2 ⌐

"Economic fundamentals remain sound" said Alan Gayle, a managing director of Trusco Capital Management in Atlanta, "though fourth-quarter growth may suffer."

"Economic fundamentals remain sound" said <annot type="Person">Alan Gayle</annot>, a managing director of <annot type="Organization">Trusco Capital Management</annot> in <annot type="Location" kind="city">Atlanta</annot>, "though fourth-quarter growth may suffer."

*FIG. 1B*
*Prior Art*

| Construct | Form |
|---|---|
| aSVO | adjective subject verb object |
| aSVaO | adjective subject verb adjective object |
| aOVaS | adjective object verb adjective subject |
| aOVS | adjective object verb subject |
| ••• | ••• |

*FIG. 3*

GENERATING NATURAL LANGUAGE TEXT SENTENCES AS TEST CASES FOR NLP ANNOTATORS WITH COMBINATORIAL TEST DESIGN

BACKGROUND OF THE INVENTION

Field of the Invention

The present invention generally relates to text annotators used in natural language processing, and more particularly to a method of generating test cases (e.g., sentences) used to test a text annotator.

Description of the Related Art

As interactions between users and computer systems become more complex, it becomes increasingly important to provide a more intuitive interface for a user to issue commands and queries to a computer system. As part of this effort, many systems employ some form of natural language processing. Natural language processing (NLP) is a field of computer science, artificial intelligence, and linguistics concerned with the interactions between computers and human (natural) languages. Many challenges in NLP involve natural language understanding, that is, enabling computers to derive meaning from human or natural language input, and others involve natural language generation allowing computers to respond in a manner familiar to a user. For example, a non-technical person may enter a natural language query in an Internet search engine, and the search engine intelligence can provide a natural language response which the user can hopefully understand. One example of an advanced computer system that uses natural language processing is the Watson™ cognitive technology marketed by International Business Machines Corp.

Text analysis is known in the art pertaining to NLP and typically uses a text annotator program to search text documents and analyze them relative to a defined set of tags. The text annotator can then generate linguistic annotations within the document to extract concepts and entities that might be buried in the text, such as extracting person, location, and organization names or identifying positive and negative sentiment. FIGS. 1A-1B illustrate one example of annotations that may be performed by a prior art text annotator. In this example an annotation takes the form <annot type="X">text</annot>, where "X" may be any of a defined set of annotation types such as Person, Organization and Location, and "text" is the particular text in the document that the "X" annotation characterizes. The text annotation is inserted into or otherwise associated with an example text to indicate or delineate the beginning and end of the annotated text. So, in the sentence "'Economic fundamentals remain sound' said Alan Gayle, a managing director of Trusco Capital Management in Atlanta, 'though fourth-quarter growth may suffer'", "Alan Gayle" is an instance of the annotation type Person, "Trusco Capital Management" is an instance of the annotation type Organization and "Atlanta" is an instance of the annotation type Location. Further to this example, annotation type Location has a feature, shown as "kind", with example possible values of "city", "state", and the like. The text annotator will accordingly annotate the sentence as follows: "'Economic fundamentals remain sound' said <annot type="Person">Alan Gayle</annot>, a managing director of <annot type="Organization">Trusco Capital Management</annot> in <annot type="Location" kind="city">Atlanta</annot>, 'though fourth-quarter growth may suffer'". In this manner, artificial intelligence programs using text analysis routines can obtain an "understanding" of the meaning of the annotated sentence. Custom annotators can be configured to identify and extract domain-specific information.

SUMMARY OF THE INVENTION

The present invention is generally directed to a method of generating test cases for a text annotator by receiving a corpus of text fragments and a description of the text annotator, determining types of inputs to the text annotator from the description, analyzing language structures in the corpus to identify sentence types and grammar constructs, and generating a first test case by performing a grammar tree transformation on a first selected fragment of the corpus based on the sentence types and the grammar constructs. A second test case can additionally be generated by replacing a starting phrase in a second selected fragment of the corpus with a substitute phrase from a dictionary associated with one of the types of inputs that corresponds to the starting phrase. The dictionary can include a false synonym for the input type that corresponds to the starting phrase for purposes of negative testing. The first test case can be generated by performing a sequence of different successive grammar tree transformations starting with the first selected fragment, and the second test case can be generated by replacing multiple starting phrases in the second selected fragment with respective substitute phrases from multiple dictionaries associated with different ones of the types of inputs that correspond to the multiple starting phrases. The two generating approaches can also be combined, for example, generating a third test case by performing another grammar tree transformation on the second test case. In an exemplary implementation at least one of the types of inputs corresponds to multiple grammar constructs.

The above as well as additional objectives, features, and advantages of the present invention will become apparent in the following detailed written description.

BRIEF DESCRIPTION OF THE DRAWINGS

The present invention may be better understood, and its numerous objects, features, and advantages made apparent to those skilled in the art by referencing the accompanying drawings.

FIGS. 1A and 1B represent an example of a conventional text annotator which inserts certain linguistic annotations into a sentence to identify defined concepts or phrase types;

FIG. 3 is a table of grammar constructs that are identified in an exemplar corpus and used to drive grammar tree transformations in accordance with one implementation of the present invention;

The use of the same reference symbols in different drawings indicates similar or identical items.

DESCRIPTION OF THE PREFERRED EMBODIMENT(S)

Text annotators are critical to systems that use natural language processing. A cognitive program can only derive an appropriate response to a command or query if it can accurately characterize the text therein. It is thus important to test a proposed NLP annotator to ensure that it can provide appropriate linguistic annotations. It is difficult to fully test an NLP annotator, however, due to the complexities of human languages, and the English language in particular. In complex domains, there may be millions of ways to express the same concept. Even in simpler domains there may be thousands of ways to describe the same concept. These problems are exacerbated when an NLP annotator is developed for a new industrial field or is using new text analysis objectives. Given the breadth of the problem space, it is difficult to come up with a full test suite for a given annotator.

Most annotator developers come up with a "scratch pad" of sentences they test against. These sentences are manually curated, gleaned from domain texts, and in some domains manually anonymized. This effort is slow, labor-intensive, error-prone, and usually stops after generating tens or hundreds of tests, orders of magnitude below what is needed for sufficiently high confidence in the annotator. It would, therefore, be desirable to devise an improved method of providing test cases for a text annotator which is both quicker and guaranteed to adequately cover the annotator. It would be further advantageous if the method could automatically generate scrubbed (anonymized) sentences in domains with sensitive information.

The present invention achieves these objectives by starting with reasoning about the annotator under test, to determine the kinds of inputs to this annotator. Additionally, the structure of all of the sentences in a reference corpus of text (having a large number of text fragments) is analyzed to learn what kind of grammar constructs are present and prevalent in the corpus, as well as what kind of constructs are not present in the corpus. This information is combined to determine what kinds of sentences to generate using natural language generation (NLG). The sentences generated by NLG form the basis of test cases for the proposed annotator.

Figure 2:
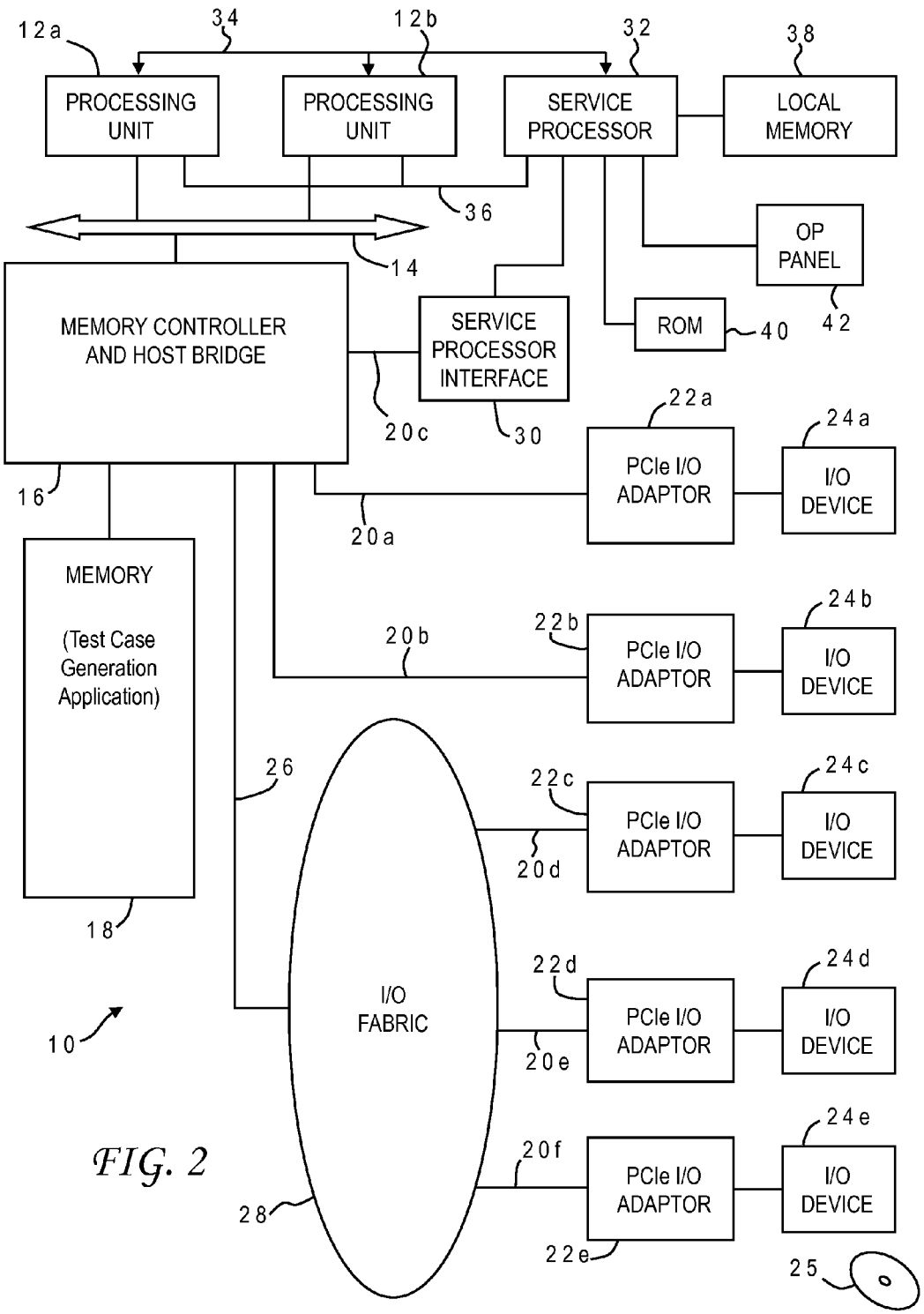
FIG. 2 is a block diagram of a computer system programmed to carry out generations of test cases for a text annotator in accordance with one implementation of the present invention.

With reference now to the figures, and in particular with reference to FIG. 2, there is depicted one embodiment 10 of a computer system in which the present invention may be implemented to carry out generation of test sentences for an NLP annotator. Computer system 10 is a symmetric multiprocessor (SMP) system having a plurality of processors 12a, 12b connected to a system bus 14. System bus 14 is further connected to and communicates with a combined memory controller/host bridge (MC/HB) 16 which provides an interface to system memory 18. System memory 18 may be a local memory device or alternatively may include a plurality of distributed memory devices, preferably dynamic random-access memory (DRAM). There may be additional structures in the memory hierarchy which are not depicted, such as on-board (L1) and second-level (L2) or third-level (L3) caches.

MC/HB 16 also has an interface to peripheral component interconnect (PCI) Express links 20a, 20b, 20c. Each PCI Express (PCIe) link 20a, 20b is connected to a respective PCIe adaptor 22a, 22b, and each PCIe adaptor 22a, 22b is connected to a respective input/output (I/O) device 24a, 24b. MC/HB 16 may additionally have an interface to an I/O bus 26 which is connected to a switch (I/O fabric) 28. Switch 28 provides a fan-out for the I/O bus to a plurality of PCI links 20d, 20e, 20f. These PCI links are connected to more PCIe adaptors 22c, 22d, 22e which in turn support more I/O devices 24c, 24d, 24e. The I/O devices may include, without limitation, a keyboard, a graphical pointing device (mouse), a microphone, a display device, speakers, a permanent storage device (hard disk drive) or an array of such storage devices, an optical disk drive which receives an optical disk 25 (one example of a computer readable storage medium) such as a CD or DVD, and a network card. Each PCIe adaptor provides an interface between the PCI link and the respective I/O device. MC/HB 16 provides a low latency path through which processors 12a, 12b may access PCI devices mapped anywhere within bus memory or I/O address spaces. MC/HB 16 further provides a high bandwidth path to allow the PCI devices to access memory 18. Switch 28 may provide peer-to-peer communications between different endpoints and this data traffic does not need to be forwarded to MC/HB 16 if it does not involve cache-coherent memory transfers. Switch 28 is shown as a separate logical component but it could be integrated into MC/HB 16.

In this embodiment, PCI link 20c connects MC/HB 16 to a service processor interface 30 to allow communications between I/O device 24a and a service processor 32. Service processor 32 is connected to processors 12a, 12b via a JTAG interface 34, and uses an attention line 36 which interrupts the operation of processors 12a, 12b. Service processor 32 may have its own local memory 38, and is connected to read-only memory (ROM) 40 which stores various program instructions for system startup. Service processor 32 may also have access to a hardware operator panel 42 to provide system status and diagnostic information.

In alternative embodiments computer system 10 may include modifications of these hardware components or their interconnections, or additional components, so the depicted example should not be construed as implying any architectural limitations with respect to the present invention. The invention may further be implemented in an equivalent cloud computing network.

When computer system 10 is initially powered up, service processor 32 uses JTAG interface 34 to interrogate the system (host) processors 12a, 12b and MC/HB 16. After completing the interrogation, service processor 32 acquires an inventory and topology for computer system 10. Service processor 32 then executes various tests such as built-in-self-tests (BISTs), basic assurance tests (BATs), and memory tests on the components of computer system 10. Any error information for failures detected during the testing is reported by service processor 32 to operator panel 42. If a valid configuration of system resources is still possible after taking out any components found to be faulty during the testing then computer system 10 is allowed to proceed. Executable code is loaded into memory 18 and service processor 32 releases host processors 12a, 12b for execution of the program code, e.g., an operating system (OS) which is used to launch applications and in particular the test case generator application of the present invention, results of which may be stored in a hard disk drive of the system (an I/O device 24). While host processors 12a, 12b are executing program code, service processor 32 may enter a mode of monitoring and reporting any operating parameters or errors, such as the cooling fan speed and operation, thermal sensors, power supply regulators, and recoverable and non-recoverable errors reported by any of processors 12a, 12b, memory 18, and MC/HB 16. Service processor 32 may take further action based on the type of errors or defined thresholds.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Computer system 10 carries out program instructions for a test case generation process that uses novel natural language processing techniques to provide large sets of test sentences for a new annotator. Accordingly, a program embodying the invention may also include conventional aspects of various text analysis tools, and these details will become apparent to those skilled in the art upon reference to this disclosure.

In a preferred implementation of the present invention, the application running on computer system 10 goes through a reasoning process regarding the annotator under test (explained in further detail below), considering the possible inputs to the annotator and the combinations of these inputs for which testing is desired by the designer, and generates or identifies dictionaries for each of these inputs. The inputs of interest form a filter over the corpus. The application then analyzes the language structures in the corpus, noting the sentence types and grammar constructs that are present and not present in the text fragments that have inputs to the annotator under test. Two sets of test fragments/sentences can be generated from the corpus, first by performing grammar manipulations on fragments to generate new fragments, and second by using NLG to generate fragments with the same structure as a found fragment.

Further to the preferred implementation, the reasoning about the annotator under test can begin by determining the inputs to the annotator Annotators generally come with "code" files and "descriptor" (metadata) files. The descriptors will explicitly list inputs and outputs. Inputs and outputs can also be extracted from the code. For example, a new annotator has been designed for providing annotations in text regarding patients having a cancer diagnosis. The application running on computer system 10 receives a computer-readable description of this cancer annotator which indicates that it uses inputs of a "person" phrase, a "diagnosis verb" phrase, a "cancer" (or "leukemia") phrase, and optionally a "date" phrase. The high level grammar constructs which each of these phrases can take are then listed, e.g., noun_phrase, noun_phrase-verb-noun_phrase, etc. The mapping to grammar constructs can be provided with descriptors or could be learned. A particular phrase might actually be triggered by more than one grammar construct, for example, a "cancer" phrase could be triggered by a noun ("tumor"), a verb ("metastasizing"), or an adjective ("cancerous").

The application embodying the present invention can further determine appropriate dictionaries that include terms for each of the grammar constructs under test. These dictionaries can be generated by the application, or can be provided by a third party having expertise in the particular domain. Appropriate dictionaries can be identified by including tags or other metadata with the dictionary which can be matched against phrase types. Each dictionary has multiple entries corresponding to a particular input type, e.g., a dictionary for a "leukemia" phrase can include "leukemia", "acute myeloid leukemia", "AML", "myelodysplastic syndrome", "MDS", etc. Each phrase in the dictionary has an associated indicator for the phrase type (grammar construct). At least one of the dictionaries preferably includes some terms which are appropriate for the annotator domain but which should not cause any annotation (false synonyms), for purpose of generating negative test cases. For example, the dictionary for the "leukemia" phrase might also include "cystic fibrosis" since that term is a medical diagnosis and so is generally consistent with the annotator domain but is not relevant to a cancer diagnosis.

An exemplar corpus can be manually generated but can also be obtained from extant sources (electronic documents) which provide textual discussions within the domain(s) of the annotator under test. The corpus is preferably scrubbed (anonymized) to remove any personal health information whose disclosure might violate privacy laws. The corpus is analyzed for grammatical structures by first scanning the text for fragments that include the input types or domain concepts relevant to the annotator. A "fragment" refers to any span of text that an annotator can operate on. Different annotators can work over different fragment lengths, the most common lengths being sentence and paragraph, although it is possible to work on larger or smaller spans. A fragment can be larger than a sentence, but a sentence can also be made up of several fragments. If the annotator has several types of inputs, the application can scan for all permutations of the inputs, or scan for a set of permutations chosen by the tester. For example, if the annotator inputs are "cancer" term, "diagnosis" term, and optional "date" term, the tester may choose to scan only for selected fragments having "cancer"+"diagnosis"+"date", "cancer"+"diagnosis", "cancer", or "diagnosis".

The selected fragments are then analyzed to distinguish any high-level grammar constructs. FIG. 3 shows several grammar constructs that might be found in a corpus. These include an adjective-subject-verb-object construct (denoted aSVO), an adjective-subject-verb-adjective-object construct (denoted aSVaO), an adjective-object-verb-adjective-subject construct (denoted aOVaS), and an adjective-object-verb-subject construct (denoted aOVS). Those skilled in the art will appreciate that many other forms for grammar constructs may be used, including more complex forms having other phrase types such as "preposition" or "adverb", and compound forms. The grammar constructs can be recognized using conventional means, such as slot grammar parsing. As the name suggests, slot grammar is based on the idea of slots, which represent syntactic roles of phrases in a sentence. Examples of slots include subject, direct object, indirect object, predicate complement, object of preposition, etc. For an English-language annotator an English slot grammar (ESG) parse is performed. All of the parse trees (corresponding to particular grammar constructs) that are found are recorded along with the number of times each fired. The application can also record trees that are not found. For example, in a medical corpus the "Question" and "Command" parse trees may never fire, but the "Compound Sentence" and "Conditional Sentence" parse trees may fire heavily. It does not make sense to generate many test cases for Command sentences if they constitute 0.2% of all sentences. The invention can accordingly be further optimized to generate more (or only) test cases having sentence types that correspond to more heavily encountered parse trees (or at least the most common parse tree), by biasing the fragment selection (or filtering) to select more of those types of fragments from the corpus for processing. In addition to sentence types, the application can also take note of parse trees for larger or smaller units. The present invention can be applied to multiple exemplar corpora, i.e., generating multiple test buckets from different corpora.

Figure 4:
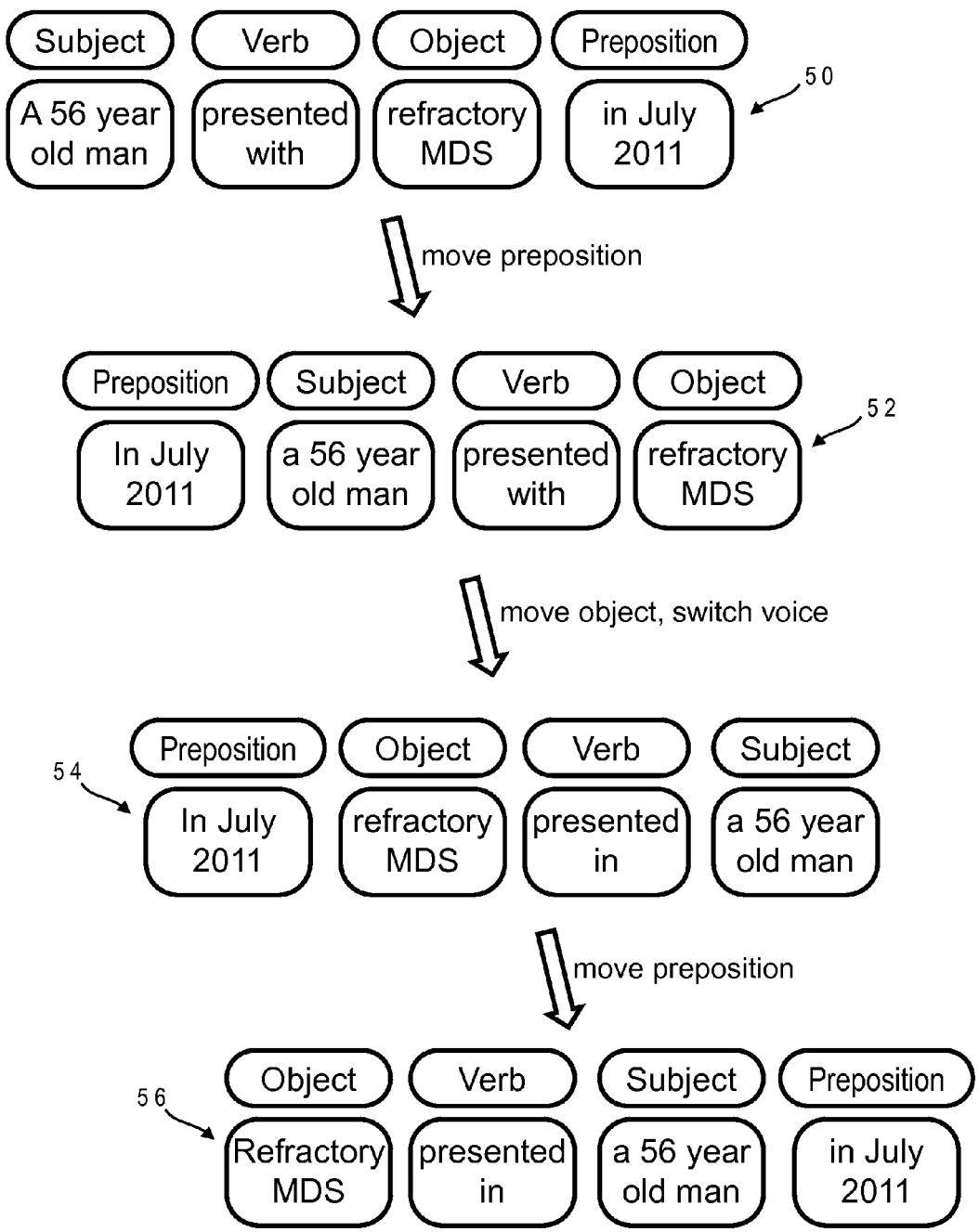
FIG. 4 is a pictorial representation of grammar tree transformations that are applied to a sentence having identified phrase types in accordance with one implementation of the present invention.

Test data can be generated from the selected fragments in either or both of two ways. First, a given fragment can be reconstructed according to legal sentence tree transformations. FIG. 4 illustrates some of the tree transformations that can be performed on a starting sentence (fragment) 50 according to a preferred implementation. Sentence 50 from the corpus states "A 56 year old man presented with refractory MDS in July 2011." This fragment is determined to be of grammar construct type subject-verb-object-preposition, wherein "A 56 year old man" is the subject phrase, "presented with" is the verb phrase, "refractory MDS" is the object phrase, and "in July 2011" is the preposition phrase. Legal tree transformations for this construct include movement of the preposition phrase to any other slot location, or movement of the object combined with a switch in voice from active to passive or vice-versa. Thus, moving the preposition phrase to the beginning of the sentence results in a first transformed sentence 52 which reads "In July 2011 a 56 year old man presented with refractory MDS." Moving the object and switching the voice (in this case, from active to passive) results in the further transformed sentence 54: "In July 2011 refractory MDS presented in a 56 year old man." "Legal" grammar transformations refer to those linguistic rules which are generally known according to the particular language; for example, one known transformation for switching voice in English is "<subject> <verb> with <object>" becomes "<object> <verb> in <subject>". A particular type of transformation can be repeated within a chain of transformations so the preposition can be moved again, in this case back to the end of the final transformed sentence 56: "Refractory MDS presented in a 56 year old man in July 2011". Final sentence 56 can then be stored as one of many test cases for the annotator. Any of these transformed sentences has high confidence of being accurately tailored for the annotator since the knowledge they represent can be found in the corpus.

Figure 5:
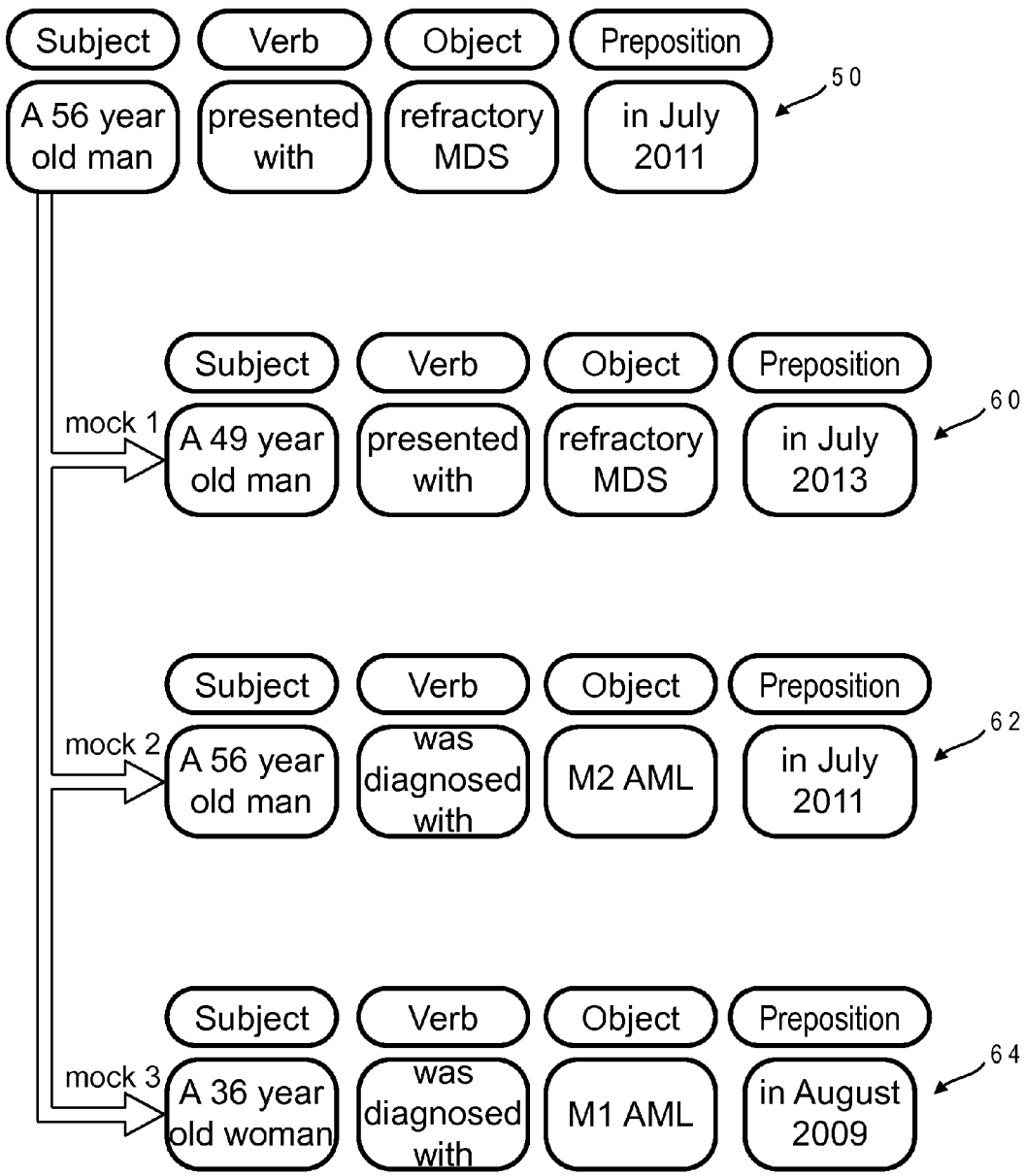
FIG. 5 is a pictorial representation of substitution transformations that are applied to a sentence having using an associated dictionary in accordance with one implementation of the present invention.

Test data can also be generated from suitable fragments by performing selected substitutions based on input types of the annotator to derive mock sentences. FIG. 5 illustrates some of the substitutions that can be performed on the same starting sentence 50 from the corpus according to a preferred implementation. In a first mock sentence 60 dictionaries for a "person" input type and a "date" input type have been employed to provide substitutions (synonyms): the subject phrase "A 56 year old man" ("person" input type) has been replaced with the subject phrase "A 49 year old man" (also "person" input type), and the preposition phrase "in July 2011" ("date" input type) has been replaced with the preposition phrase "in July 2013" (also "date" input type). In a second mock sentence 62 dictionaries for a "diagnosis verb" input type and a "leukemia" input type have been employed to provide substitutions: the verb phrase "presented with" ("diagnosis verb" input type) has been replaced with the verb phrase "was diagnosed with" (also "diagnosis verb" input type), and the object phrase "refractory MDS" ("leukemia" input type) has been replaced with the object phrase "M2 AML" (also "leukemia" input type). In a third mock sentence 64 dictionaries for all four input types have been employed to provide complete substitutions: the subject phrase "A 56 year old man" has been replaced with the subject phrase "A 36 year old woman", the verb phrase "presented with" has been replaced with the verb phrase "was diagnosed with", the object phrase "refractory MDS" has been replaced with the object phrase "M1 AML", and the preposition phrase "in July 2011" has been replaced with the preposition phrase "in August 2009". Any of these substitution sentences can again be stored as test cases for the annotator.

Figure 6:
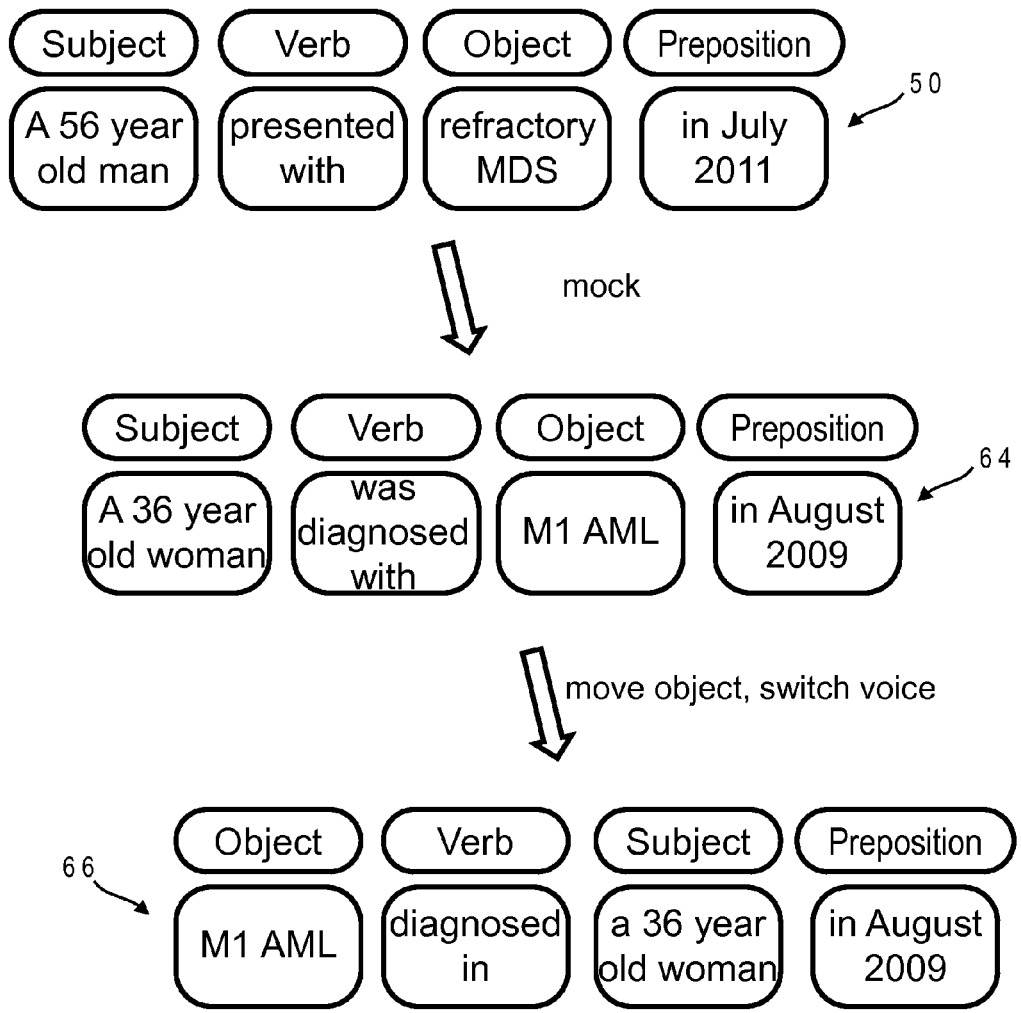
FIG. 6 is a pictorial representation of a combination of a grammar tree transformation similar to that of FIG. 4 and a substitution transformation similar to that of FIG. 5 that are applied to a sentence in accordance with one implementation of the present invention.

These two different approaches can be combined as illustrated in FIG. 6. Beginning with the same starting sentence 50, substitutions are made to derive a mock sentence 64 as in FIG. 5 (making substitutions for all of the input types in the fragment). Mock sentence 64 is now used as an input to a tree transformation which moves the object and switches voice, resulting in the transformed sentence (test case) 66: "M1 AML diagnosed in a 36 year old woman in August, 2009". While FIG. 6 illustrates only one transformation and one substitution in the sentence chain, any number of transformations and substitutions can be implemented according to the preferences of the tester. The particular order of the transformations/substitutions in a sequence is not determinative since the operations are commutative. The exact transformations and substitutions used on any particular corpus fragment may be selected interactively by the tester, selected according to predetermined (programmed) selection routines, or simply by randomly selecting a transformation or substitution from those available with the input types and grammar constructs.

Figure 7:
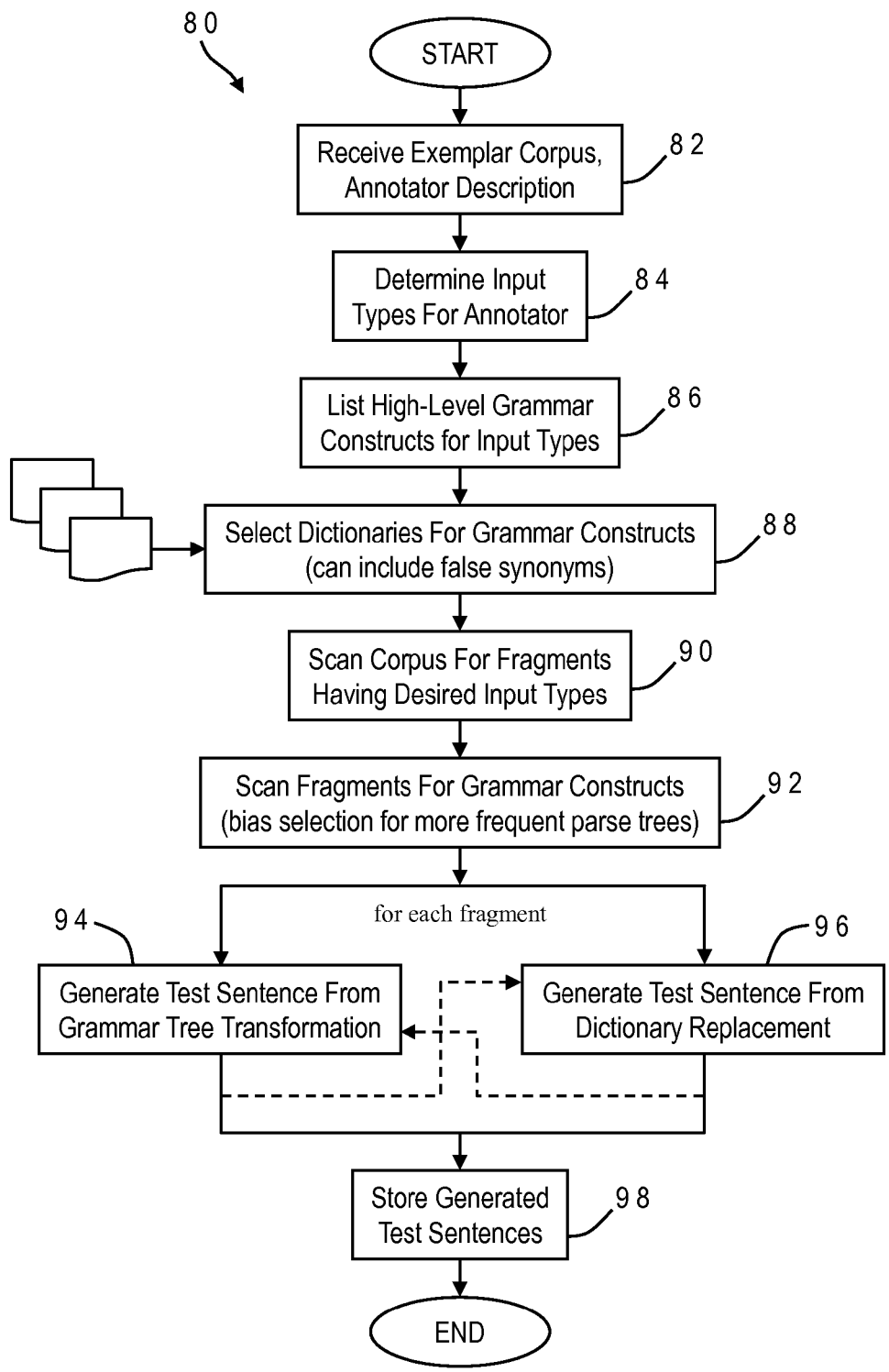
FIG. 7 is a chart illustrating the logical flow for a test case generator in accordance with one implementation of the present invention.

The present invention may be further understood with reference to the chart of FIG. 7 which shows a test case generation process 80 in accordance with an exemplary embodiment. Process 80 begins when the application running on computer system 10 (or other system implementing the invention) receives an exemplar corpus and a description of the annotator to be tested (82). Input types are determined for the annotator (84), and a list is created of grammar constructs for fragments in the corpus having the input types (86). Dictionaries are selected as appropriate based on the grammar constructs (88). As noted above, the dictionaries may include terms which should not be annotated for negative testing. The corpus is scanned for any fragments having the input types as selected by the tester (90). Those fragments are further scanned to determine their grammar constructs (92), e.g., using an ESG parse. As noted above, fragment selection can be biased to include more sentence types corresponding to the most heavily encountered parse trees in the corpus. For each selected fragment, one or more test sentences are generated using grammar tree transformations (94) and one or more additional test sentences are generated using dictionary replacements (96), or some combination of tree transformation and dictionary replacement. Each of these generated test sentences is stored in the test bucket (98) to be used during later testing of the annotator. The invention thereby provides the benefit of automatically generating large and complete sets of test cases for NLP annotators.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that such modifications can be made without departing from the spirit or scope of the present invention as defined in the appended claims.

What is claimed is:

1. A method of generating test cases for a text annotator which searches text documents and analyzes them relative to a defined set of tags comprising:
   receiving a corpus of text fragments without any annotations and a description of the text annotator, by executing first instructions in a computer system;
   determining types of inputs to the text annotator from the description, the types of inputs including at least one phrase selected from the group consisting of a person phrase, a date phrase, and a diagnosis phrase, by executing second instructions in the computer system;
   analyzing language structures in the corpus to identify sentence types and grammar constructs, the sentence types including at least one sentence selected from the group consisting of a question, a command, a compound sentence, and a conditional sentence, and wherein said analyzing includes performing a slot grammar parse of the corpus to determine various parse trees of the corpus including a most common parse tree, by executing third instructions in the computer system;

generating a first test case by performing a grammar tree transformation on a first selected fragment of the corpus based on the sentence types and the grammar constructs wherein the first selected fragment is selected in response to a selection bias towards a sentence type which corresponds to the most common parse tree of the corpus, by executing fourth instructions in the computer system; and generating a second test case by replacing at least one starting phrase in the first test case with a substitute phrase from at least one dictionary associated with one of the types of inputs that corresponds to the starting phrase, by executing fifth instructions in the computer system.

2. The method of claim 1 wherein the first test case is generated by performing a sequence of different successive grammar tree transformations starting with the first selected fragment.

3. The method of claim 1 wherein the second test case is generated by replacing multiple starting phrases in the second selected fragment with respective substitute phrases from multiple dictionaries associated with different ones of the types of inputs that correspond to the multiple starting phrases.

4. The method of claim 1 wherein at least one of the types of inputs corresponds to multiple grammar constructs.

5. The method of claim 1 wherein the dictionary includes a false synonym for the one input type that corresponds to the starting phrase.

6. The method of claim 1 further comprising testing the text annotator using the first and second test cases.

7. A computer system comprising:
one or more processors which process program instructions;
a memory device connected to said one or more processors; and
program instructions residing in said memory device for generating test cases for a text annotator which searches text documents and analyzes them relative to a defined set of tags by receiving a corpus of text fragments without any annotations and a description of the text annotator, determining types of inputs to the text annotator from the description wherein the types of inputs include at least one phrase selected from the group consisting of a person phrase, a date phrase, and a diagnosis phrase, analyzing language structures in the corpus to identify sentence types and grammar constructs wherein the sentence types include at least one sentence selected from the group consisting of a question, a command, a compound sentence, and a conditional sentence, and the analyzing includes performing a slot grammar parse of the corpus to determine various parse trees of the corpus including a most common parse tree, generating a first test case by performing a grammar tree transformation on a first selected fragment of the corpus based on the sentence types and the grammar constructs wherein the first selected fragment is selected in response to a selection bias towards a sentence type which corresponds to the most common parse tree of the corpus, and generating a second test case by replacing at least one starting phrase in the first test case with a substitute phrase from at least one dictionary associated with one of the types of inputs that corresponds to the starting phrase.

8. The computer system of claim 7 wherein the first test case is generated by performing a sequence of different successive grammar tree transformations starting with the first selected fragment.

9. The computer system of claim 7 wherein the second test case is generated by replacing multiple starting phrases in the second selected fragment with respective substitute phrases from multiple dictionaries associated with different ones of the types of inputs that correspond to the multiple starting phrases.

10. The computer system of claim 7 wherein at least one of the types of inputs corresponds to multiple grammar constructs.

11. The computer system of claim 7 wherein the dictionary includes a false synonym for the one input type that corresponds to the starting phrase.

12. The computer system of claim 7 wherein said program instructions further test the text annotator using the first and second test cases.

13. A computer program product comprising:
a computer readable storage medium; and
program instructions residing in said storage medium for generating test cases for a text annotator which searches text documents and analyzes them relative to a defined set of tags by receiving a corpus of text fragments without any annotations and a description of the text annotator, determining types of inputs to the text annotator from the description wherein the types of inputs include at least one phrase selected from the group consisting of a person phrase, a date phrase, and a diagnosis phrase, analyzing language structures in the corpus to identify sentence types and grammar constructs wherein the sentence types include at least one sentence selected from the group consisting of a question, a command, a compound sentence, and a conditional sentence, and the analyzing includes performing a slot grammar parse of the corpus to determine various parse trees of the corpus including a most common parse tree, generating a first test case by performing a grammar tree transformation on a first selected fragment of the corpus based on the sentence types and the grammar constructs wherein the first selected fragment is selected in response to a selection bias towards a sentence type which corresponds to the most common parse tree of the corpus, and generating a second test case by replacing at least one starting phrase in the first test case with a substitute phrase from at least one dictionary associated with one of the types of inputs that corresponds to the starting phrase.

14. The computer program product of claim 13 wherein the first test case is generated by performing a sequence of different successive grammar tree transformations starting with the first selected fragment.

15. The computer program product of claim 13 wherein the second test case is generated by replacing multiple starting phrases in the second selected fragment with respective substitute phrases from multiple dictionaries associated with different ones of the types of inputs that correspond to the multiple starting phrases.

16. The computer program product of claim 13 wherein at least one of the types of inputs corresponds to multiple grammar constructs.

17. The computer program product of claim 13 wherein the dictionary includes a false synonym for the one input type that corresponds to the starting phrase.

18. The computer program product of claim 13 wherein said program instructions further test the text annotator using the first and second test cases.

\* \* \* \* \*